(12) United States Patent
Kurnik

(10) Patent No.: US 9,607,128 B2
(45) Date of Patent: Mar. 28, 2017

(54) DETECTION AND CORRECTION OF JUMPS IN REAL-TIME PCR SIGNALS

(71) Applicant: Roche Molecular Systems, Inc., Pleasanton, CA (US)

(72) Inventor: Ronald T. Kurnik, Foster City, CA (US)

(73) Assignee: Roche Molecular Systems, Inc., Pleasanton, CA (US)

(*) Notice: Subject to any disclaimer, the term of this patent is extended or adjusted under 35 U.S.C. 154(b) by 597 days.

(21) Appl. No.: 14/144,382

(22) Filed: Dec. 30, 2013

(65) Prior Publication Data

US 2015/0186598 A1 Jul. 2, 2015

(51) Int. Cl.

| | | |
|---|---|---|
| *G01C 19/00* | (2013.01) | |
| *G01C 25/00* | (2006.01) | |
| *G01D 18/00* | (2006.01) | |
| *G01F 19/00* | (2006.01) | |
| *G06F 19/00* | (2011.01) | |
| *G06F 19/28* | (2011.01) | |

(Continued)

(52) U.S. Cl.
CPC ............ *G06F 19/28* (2013.01); *C12Q 1/686* (2013.01); *G06F 19/24* (2013.01)

(58) Field of Classification Search
CPC .... A61K 2300/00; A61K 45/06; A61K 31/43; A61K 31/431; A61K 38/179; A61K 31/513; A61K 31/675; A61K 31/704; A61K 31/7042; A61K 2039/505; A61K 31/337; A61K 38/00; A61K 39/3955; G06F 19/10; G06F 19/24; G06F 19/18; G06F 19/20; G06F 19/22; G06F 17/10; G06F 17/30386; G06F 17/17; G06F 17/18; G06F 17/5009; G06F 19/28; G01F 23/24; G01F 23/26

See application file for complete search history.

(56) References Cited

U.S. PATENT DOCUMENTS

| | | |
|---|---|---|
| 2,997,704 A | 8/1961 | Gordon et al. |
| 8,285,489 B2 | 10/2012 | Lerner |
| 8,374,795 B2 | 2/2013 | Sane |

(Continued)

OTHER PUBLICATIONS

Anderson, E. et al., "Lapack Users' Guide," Third Edition, 1999, located at <http://www.netlib.org/lapack/lug/index.html>, last visited on Aug. 4, 2008, Table of Contents, 5 pages.

(Continued)

*Primary Examiner* — Roy Y Yi
(74) *Attorney, Agent, or Firm* — Kilpatrick Townsend & Stockton LLP

(57) ABSTRACT

Systems, methods, and apparatuses are provided for detecting and potentially invalidating or correcting jump errors in data from growth processes. A jump error can be identified by determining a second derivative of the data set, and identifying two consecutive cycles with opposite signs in the second derivative. Once a jump error has been detected, the data set can be invalidated or corrected based on various criteria. Whether to invalidate or correct can be based on an absolute jump height, a relative jump height (e.g., relative to the net growth or relative to the baseline), an absolute location (cycle number) of the jump, or a relative location. In one implementation, the jump can be corrected by subtracting a jump height from points subsequent to the jump or by adding the jump height to points prior to the jump.

20 Claims, 12 Drawing Sheets

(51) Int. Cl.
    *C12Q 1/68*     (2006.01)
    *G06F 19/24*     (2011.01)

(56) References Cited

U.S. PATENT DOCUMENTS

| | | |
|---|---|---|
| 2007/0143070 A1 | 6/2007 | Kurnik et al. |
| 2007/0143385 A1* | 6/2007 | Kurnik .................... G06F 17/10 708/290 |
| 2007/0148632 A1 | 6/2007 | Kurnik et al. |
| 2009/0119020 A1 | 5/2009 | Kurnik et al. |
| 2010/0070190 A1* | 3/2010 | Lerner .................... G06F 17/10 702/19 |

OTHER PUBLICATIONS

Burnham, K.P. et al., Model Selection and Multimodel Inference: A Practical-Theoretic Approach, 2nd Edition, Springer: NY, 2002, Table of Contents, 10 pages.

More, J.J., "The Levenberg-Marquardt Algorithm: Implementation and Theory," Numerical Analysis, Watson, G,A, ed., Lecture Notes in Mathematics 630, Springer-Verlag, 1977, pp. 105-116.

Press, W.H. et al., Numerical Recipes in C: The Art of Scientific Computing, 2nd Edition, Press Syndicate of the University of Cambridge: New York, 2002, Table of Contents, 8 pages.

Wang, S-S. et al., "Homogenous Real-Time Detection of Single-Nucleotide Polymorphisms by Strand Displacement Amplification on the BD ProbeTec ET System," Clinc. Chem., 2003, vol. 49, No. 10, p. 1599.

Weissten, E.W., "Jacobian," Mathworld—A Wolfram Web Resource, 1999-2008 located at <http://mathworld.wolfram.com. Jacobian.html>, last accessed on Oct. 31, 2008, 4 pages.

Weisstein, E.W., "Vandermonde Matrix," Mathworld—A Wolfram Web Resource, 1999-2008, located at <http://mathworld.wolfram.com/Vandermonde Matrix.html>, last accessed on Oct. 31, 2008, 3 pages.

Weusten, J.J.A.M. et al., "Principles of Quantitation of Viral Loads Using Nucleic Acid Sequence-Based Amplification in Combination With Homogenous Detection Using Molecular Beacons," Nucleic Acids Research, 2002, vol. 30, No. 6, p. 26.

* cited by examiner

FIG. 1A
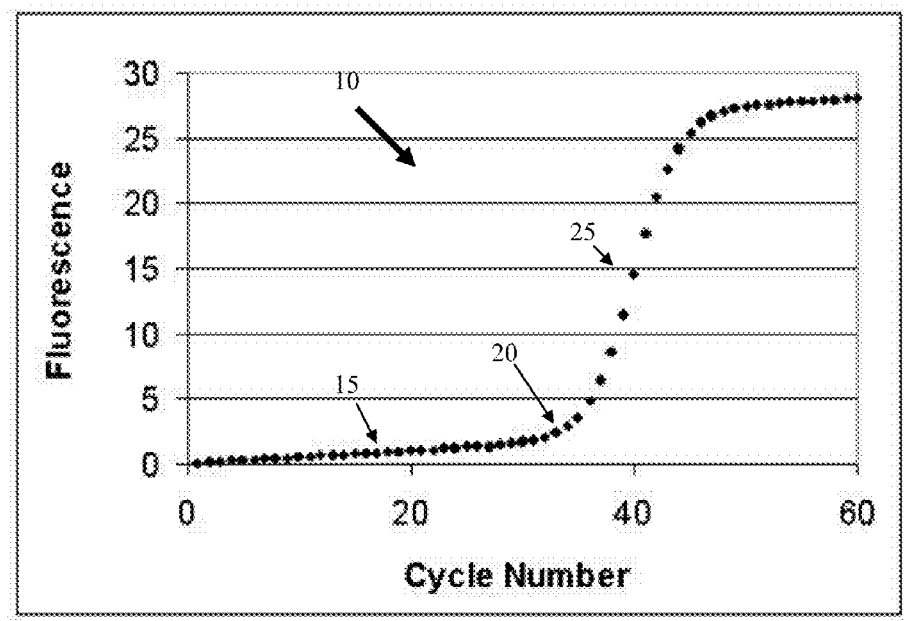
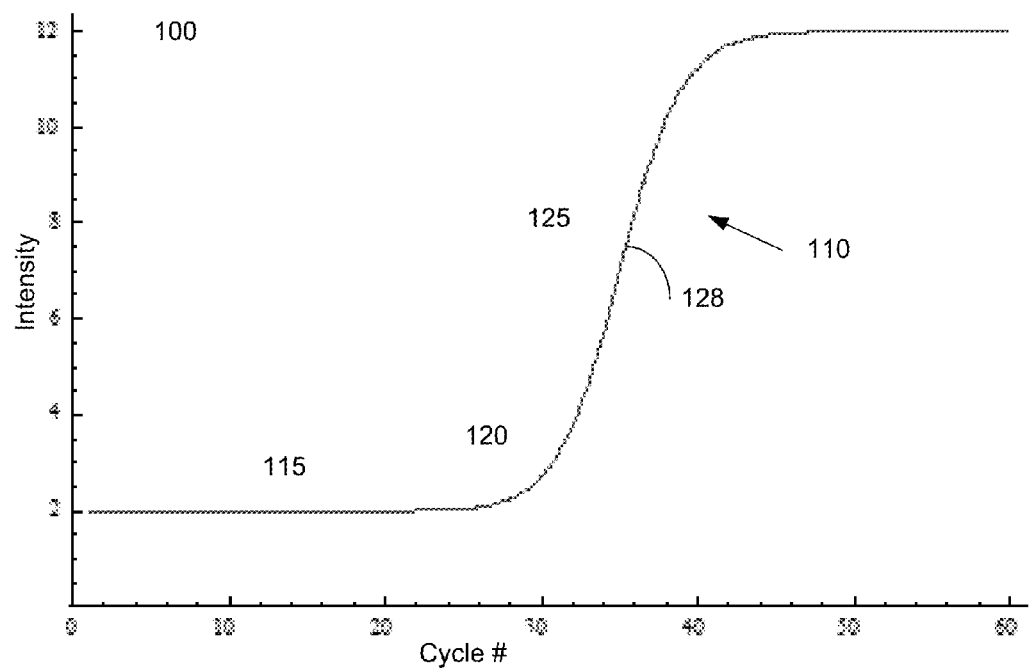
FIG. 1B

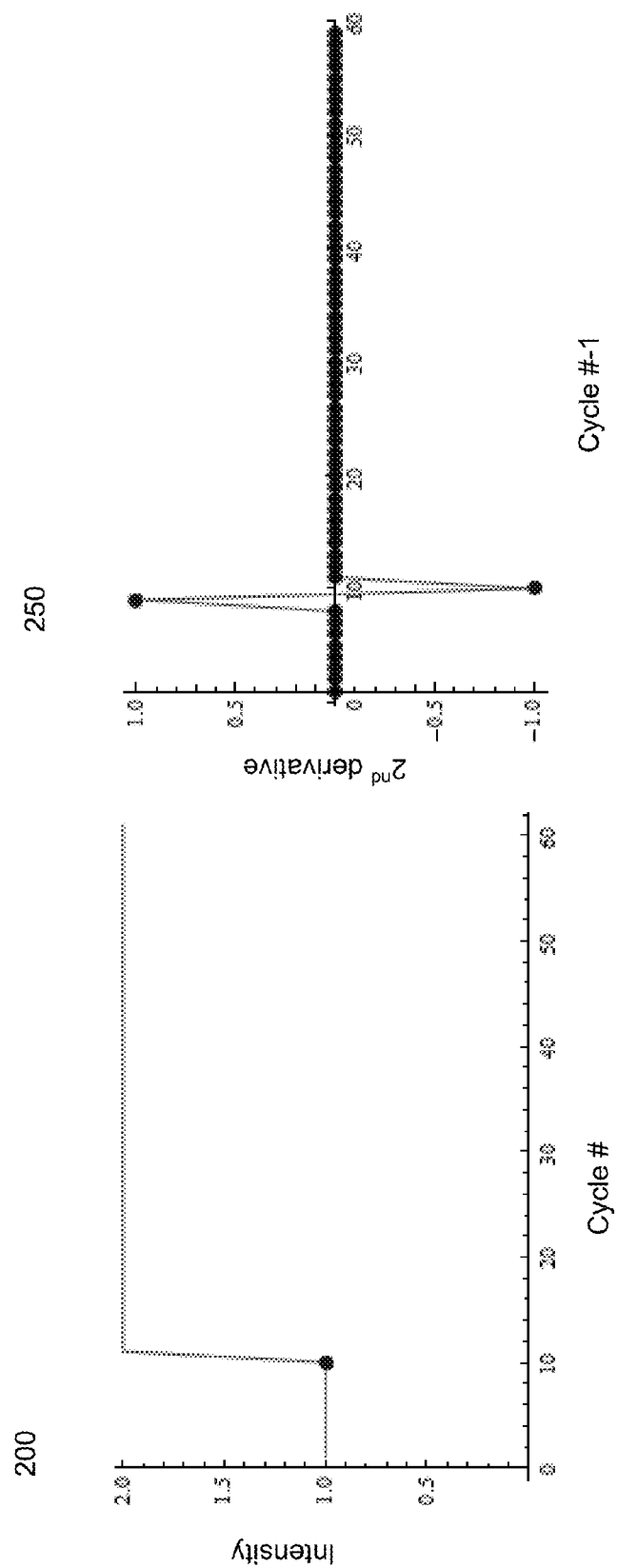

US 9,607,128 B2

DETECTION AND CORRECTION OF JUMPS IN REAL-TIME PCR SIGNALS

FIELD

The present disclosure relates generally to systems and methods for processing data resulting from a growth process (e.g., PCR or bacterial) of a sample, and more particularly to systems and methods for detecting jump errors.

BACKGROUND

The Polymerase Chain Reaction (PCR) is an in vitro method for enzymatically synthesizing or amplifying defined nucleic acid sequences. The reaction typically uses two oligonucleotide primers that hybridize to opposite strands and flank a template or target DNA sequence that is to be amplified. Elongation of the primers is catalyzed by a heat-stable DNA polymerase. A repetitive series of cycles involving template denaturation, primer annealing, and extension of the annealed primers by the polymerase provides an exponential accumulation of a specific DNA fragment. Fluorescent probes or markers are typically used in the process to facilitate detection and quantification of the amplification process A typical kinetic PCR curve is shown in FIG. 1A, where fluorescence intensity values are plotted vs. cycle number for a typical PCR process. In this case, the formation of PCR products is monitored in each cycle of the PCR process. The amplification is usually measured in thermocyclers which include components and devices for measuring fluorescence signals during the amplification reaction. An example of such a thermocycler is the Roche Diagnostics LightCycler (Cat. No. 20110468). The amplification products are, for example, detected by means of fluorescent labeled hybridization probes which only emit fluorescence signals when they are bound to the target nucleic acid or in certain cases also by means of fluorescent dyes that bind to double-stranded DNA.

However, errors can arise in the data, thereby causing errors in the analysis of the data and resulting physical properties (e.g., quantification of starting material) obtained from the analysis. One particular type of error is a jump error. The cause of these jumps may be due to air bubbles, droplets on cover film, altered meniscus, particulates, thermal, or other issues.

Therefore it is desirable to provide systems and methods for detecting and potentially correcting jump errors in data from growth processes.

BRIEF SUMMARY

Systems, methods, and apparatuses are provided for detecting and potentially invalidating or correcting jump errors in data from growth processes. Embodiments can identify a jump error by determining a second derivative of the data set, and identifying two consecutive cycles with opposite signs in the second derivative. Once a jump error has been detected, the data set can be invalidated or corrected based on various criteria. Whether to invalidate or correct can be based on an absolute jump height, a relative jump height (e.g., relative to the net growth or relative to the baseline), an absolute location (cycle number) of the jump, or a relative location (e.g., relative to a region of the growth curve, such as the baseline or exponential phase). In one implementation, the jump can be corrected by subtracting a jump height from points subsequent to the jump or by adding the jump height to points prior to the jump.

Other embodiments are directed to systems and computer readable media associated with methods described herein.

A better understanding of the nature and advantages of the present invention may be gained with reference to the following detailed description and the accompanying drawings.

BRIEF DESCRIPTION OF THE DRAWINGS

FIG. 1A illustrates an example of a typical PCR growth curve, plotted as fluorescence intensity vs. cycle number. FIG. 1B is a simulated real-time PCR curve according to embodiments of the present invention.

FIG. 2A shows a plot 200 of data from a growth process, where the data exhibits a jump error. FIG. 2B shows a plot 250 of a second derivative of a growth curve according to embodiments of the present invention.

DETAILED DESCRIPTION

Figure 3:
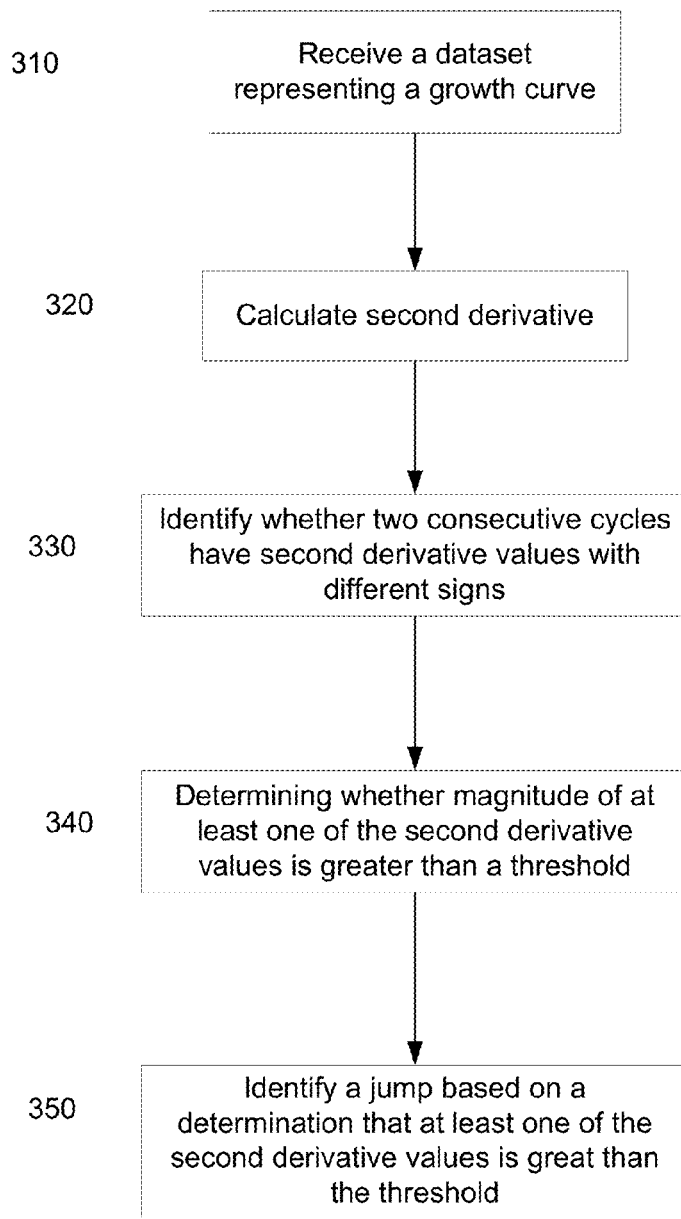
FIG. 3 is a flowchart of method 300 of detecting jump errors in a growth curve of a growth process according to embodiments of the present invention.

Embodiments can detect jumps (of varying heights) in Real-Time PCR signals (or in data from other growth processes) that occur at random cycle numbers. The cause of these jumps may be due to air bubbles, droplets on cover film, altered meniscus, particulates, thermal, biochemistry, or other issues. Although these jumps are very rare, they have the potential of giving an inaccurate cycle-threshold (CT) values, and thus can be either invalidated or corrected. Various techniques for correction of a jump error are provided. Further, the decision to invalidate or correct can be made based on various criteria.

I. Growth Curves

One example of an amplification curve 10 in the context of a kinetic PCR process is shown in FIG. 1A. As shown, the curve 10 includes a lag phase region 15, and an exponential phase region 25. Lag phase region 15 is commonly referred to as the baseline or baseline region. Such a curve includes a transition region 20 linking the lag phase and the exponential phase. Region 20 is commonly referred to as the elbow or elbow region. The elbow region typically defines an end to the baseline and a transition in the growth or amplification rate of the underlying process. Identifying a specific transition point in region 20 can be useful for analyzing the behavior of the underlying process.

In a typical PCR curve, identifying a transition point referred to as the elbow value or cycle threshold (Ct) value is extremely useful for understanding efficiency characteristics of the PCR process. For example, the Ct value can be used to provide quantization of the amount of DNA present in the sample being analyzed. Quantization is obtained by performing a calibration curve of the Log(DNA Amount) vs. Ct value. Subsequent samples can then use Ct values along with the calibration curve to directly obtain estimates of DNA in a sample. Ct values can also be used to provide qualitative information on the DNA sample. The Ct can be affected by a jump error, e.g., by the jump error erroneously being identified as an exponential phase region.

Other processes that may provide similar growth curves (e.g., of sigmoid shape) include bacterial processes, enzymatic processes and binding processes. In bacterial growth curves, for example, the transition point of interest has been referred to as the time in lag phase, $\lambda$. Other specific processes that produce data curves that may be analyzed according to the present invention include strand displacement amplification (SDA) processes, nucleic acid sequence-based amplification (NASBA) processes and transcription mediated amplification (TMA) processes. Examples of SDA and NASBA processes and data curves can be found in Wang, Sha-Sha, et al., "Homogeneous Real-Time Detection of Single-Nucleotide Polymorphisms by Strand Displacement Amplification on the BD ProbeTec ET System," Clin Chem 2003 49(10):1599, and Weusten, Jos J. A. M., et al., "Principles of Quantitation of Viral Loads Using Nucleic Acid Sequence-Based Amplification in Combination With Homogeneous Detection Using Molecular Beacons," Nucleic Acids Research, 2002 30(6):26, respectively, both of which are hereby incorporated by reference. Thus, although the remainder of this document will discuss embodiments and aspects of the invention in terms of its applicability to PCR curves, it should be appreciated that the present invention may be applied to data curves related to other processes.

As shown in FIG. 1A, data for a typical PCR growth curve can be represented in a two-dimensional coordinate system, for example, with PCR cycle number defining the x-axis and an indicator of accumulated polynucleotide growth defining the y-axis. Typically, the indicator of accumulated growth is a fluorescence intensity value as the use of fluorescent markers is perhaps the most widely used labeling scheme. However, it should be understood that other indicators may be used depending on the particular labeling and/or detection scheme used. Examples of other useful indicators of accumulated signal growth include luminescence intensity, chemiluminescence intensity, bioluminescence intensity, phosphorescence intensity, charge transfer, voltage, current, power, energy, temperature, viscosity, light scatter, radioactive intensity, reflectivity, transmittance, and absorbance. All such examples fall under a signal strength. The definition of cycle can also include time, process cycles, unit operation cycles and reproductive cycles.

FIG. 1B shows a plot 100 with a simulated real-time PCR curve 110. PCR curve 110 has cycle number on the horizontal (x) axis and intensity (e.g., fluorescence) on the vertical (y) axis. PCR curve 110 has a well-defined baseline 115. As shown, baseline 115 is a horizontal line at intensity (y) equal to two. For ease of presentation, there is no slope to simulated baseline 115. However, a baseline may have any linear form with a slope. Elbow region 120 lies between baseline 115 and exponential phase region 125. Exponential phase region 125 includes inflexion point 128 where PCR curve 110 begins to curve downward, as opposed to upward in elbow region 120.

Although PCR growth curve 110 is simulated, a PCR growth curve can be determined from data points of intensity taken at each cycle. A particular functional form can be assumed, and parameters can be determined such that the particular functional form approximates the data point. In some embodiments, a double sigmoid function with parameters determined by a Levenberg-Marquardt (LM) regression process can be used to find an approximation to the data points. In other embodiments, other functional forms may be used, e.g., interpolation using polynomials with continuous boundary conditions (e.g., continuous up to the second derivative) as may occur in finite element analysis, a single sigmoid function, or any set of one or more functions with a continuous second derivative across the regions of interest. In one aspect, the curve approximation and parameters can be used to pre-process the data signal, e.g., to normalize the data signal and/or to remove spikes or outlier data points as may be present in the data signal.

Even without the detection of a jump, one could still fit the data (e.g., with a double sigmoid). Depending on the size of the jump and location of the jump, the functional fit might be satisfactory, and reliable results might be obtained; however, problems can be more pronounced in certain situations. For example, the problem becomes more pronounced if there is a jump on a flat curve or a curve that would otherwise have a negative slope. In such a situation, the jump may be detected as corresponding to positive growth, which results in a false positive. As another example, a process that does have actual growth could have a quantitative value (e.g., $C_t$ value) in error when the jump is high and/or the jump occurs in the growth region. Thus, the functional form fit to the data points can show errors when the underlying data has errors, e.g., jump errors. The detection of a jump can prevent the use of erroneous data, and prevent an erroneous diagnosis or conclusion for a biological sample used in the growth process.

II. Jumps

A jump error shows up as a very large increase in the signal strength. Embodiments can be used to automate the process of detecting jump errors. Thus, embodiments can formulate techniques for allowing a computer system to automatically detect a jump error.

FIG. 2A shows a plot 200 of data from a growth process, where the data exhibits a jump error. As with FIGS. 1A and 1B, the vertical axis is intensity and the horizontal axis is cycle number (X). Plot 200 shows a flat line, with a jump at X=10. Without this jump, the data set would be otherwise flat. Thus, if a functional fit was performed, the fit may erroneously identify growth (e.g., amplification in a PCR process) at the location of the random jump, even though no growth has actually occurred. Thus, if a qualitative analysis was performed to identify whether or not growth has occurred, the qualitative analysis would be incorrect in such situations.

Problems can also arise in data sets corresponding to processes where growth has actually occurred, particularly when quantitative data is obtained. On curves where quantitative data is obtained, the functional fit can be skewed to change a location of the elbow region and the exponential region. In such situations, the Ct can be incorrect.

III. Detection of Jumps

Embodiments can use the second derivative of the growth curve to identify a jump error. Specifically, embodiments can perform a discrete calculation of the second derivative, such that a second derivative value is obtained at each cycle number. The second derivative can be calculated via a convolution of the second derivative kernel with the data set. The second derivative values can be analyzed to identify behavior representative of a jump error.

FIG. 2B shows a plot 250 of a second derivative of a growth curve according to embodiments of the present invention. The vertical axis is the value of the second derivative. The horizontal axis (x) is cycle number minus one. The second derivative at cycle number X is determined using a central fine different scheme, which uses values at cycle numbers before and after cycle number X. In embodiments using values at previous cycle numbers, the second derivative cannot be determined for the very first cycle number, and thus the first cycle number is not shown in plot 250. Accordingly, the value of nine on the horizontal axis would correspond to cycle 10. In some implementations, the second derivative at the first cycle number can be assumed to be zero, which can be inserted at the beginning of the second derivative values, thereby padding second derivative values so that the horizontal axis can correspond to cycle number.

In plot 250, detection of jumps can be determined by examination of the two outliers at x=9 and x=10. At x=9, the second derivative has a largest positive value. At x=10, the second derivative has largest negative value. In one embodiment, a rule of jump detection is that if there are two consecutive points in the second derivative graph, one positive and one negative, then a jump can be identified. In one implementation, the magnitude of these points can be required to have the highest and lowest of all points in the graph. The jump can be identified as occurring at one plus the x-value of where the highest point occurs (which is a reflection of the horizontal axis being the cycle number minus 1). Thus, in FIG. 2B, it can be inferred that the jump occurred at x=1+9=10.

A. Method

FIG. 3 is a flowchart of method 300 of detecting jump errors in a growth curve of a growth process according to embodiments of the present invention. Method 300 can be performed partially or entirely by a computer system. Certain blocks of method 300 can be omitted. An examples growth process is real-time PCR amplification. Other growth processes include bacterial processes, enzymatic processes and binding processes. Growth processes can be measured by a series of points, with each data point providing a signal strength at a cycle number.

At block 310, a dataset representing a growth curve is received. The dataset includes a plurality of data points. Each data point has a pair of coordinate values {a cycle number, a signal strength of the growth process at the cycle number}. For example, each data point in FIG. 1A is designated by a fluorescence intensity and a cycle number. Other types of signal strengths, including other types of intensities, are mentioned herein.

At block 320, a second derivative of the data set is calculated. For example, a discrete convolution of a kernel with the dataset can be calculated to obtain a second derivative of the dataset at the cycle numbers. The kernel can be any suitable set of values to be applied to the data set. For instance, to determine the second derivative at X, the kernel can be three values (e.g., 1, −2, 1), which are respectively multiplied by X−1, X, and X+1 and then summed to obtain the second derivative at X. In other embodiments, the kernel can consist of more than three values, e.g., higher odd integers such as five and seven. The kernel can be applied successively to determine the second derivative from the second cycle to the second to last cycle in the example provided above.

At block 330, it is identified whether two consecutive cycle numbers have values for the second derivative that have different signs. The second derivative for a first cycle (i.e., the first of the two consecutive cycles) can have a first value that is positive, and the second derivative for a second cycle can have a second value that is negative. Alternatively, the first value can be negative and the second value be positive. In one embodiment, the identification can be done sequentially starting from the beginning or end of the data set. In some implementations, more than one pair of consecutive cycle numbers can be identified as having different signs. Various criteria can be used to determine whether all, some, or just one of such pairs of consecutive cycle numbers should be analyzed further.

At block 340, it is determined whether a magnitude of at least one of the first value and the second value is greater than a threshold. The same threshold can be used for both the first and second values, or different thresholds can be used for each of the first and second values. This comparison to a threshold can be made when a first cycle number and a second cycle number respectively have a first value and a second value for the second derivative with different signs, as determined and block 330. Criteria can be used to select pairs of consecutive cycles having different signs when more than one pair has different signs, e.g., by use of the threshold.

In one embodiment, the threshold tests that the positive value is a largest positive value for the second derivative and a negative value is a largest negative value for the second derivative. As can be seen in FIG. 2B, the positive value is 1, which is clearly larger than any of the other values (almost all of which are close to zero). And, the negative value is −1, which is also clearly has a larger magnitude than any other negative values. Predetermined values for the threshold can also be used, e.g., based on empirical evidence of jump errors and instances associated with accurate growth data.

At block 350, a jump error is identified in the dataset representing the growth curve based on a determination that the magnitude of at least one of the first value and the second value is greater than the threshold. In one embodiment, both the first value and the second value can be required to be above a threshold (which may be the same or different for the respective values). In addition to a magnitude being greater than a threshold, other criteria can be used. For example, a location (i.e., cycle number) of the jump error can be used. Other criteria can also be used to determine any additional actions to be taken. For example, the data set can be invalidated or corrected when a jump error is identified.

In the case where method 300 is implemented in an intelligence module (e.g., processor executing instructions) resident in a PCR data acquiring device such as a thermocycler, the data set may be provided to the intelligence module in real time as the data is being collected, or it may be stored in a memory unit or buffer and provided to the intelligence module after the experiment has been completed. Similarly, the data set may be provided to a separate system such as a desktop computer system or other computer system, via a network connection (e.g., LAN, VPN, intranet, Internet, etc.) or direct connection (e.g., USB or other direct wired or wireless connection) to the acquiring device, or provided on a portable medium such as a CD, DVD, floppy disk or the like. In certain aspects, the data set includes data points having a pair of coordinate values (or a 2-dimensional vector). For PCR data, the pair of coordinate values typically represents the cycle number and the fluorescence intensity value B. Second Derivative (Convolution)

As described above, the second derivative can be calculated as a convolution of a kernel and the data set. The convolution can be implemented as a finite difference between signal values at neighboring cycles. Various kernels can be used, as will be apparent to one skilled in the art and as described below.

As an example, consider the convolution of kernel $\{x, y, z\}$ with the nine member list $\{a, b, c, d, e, f, g, h, i\}$ representing a data set from a growth process, as shown in equation (1) below.

$$ListConvolve[\{x,y,z\},\{a,b,c,d,e,f,g,h,i\}] \quad (1)$$

The result of this convolution is given by the seven member list shown in equation (2) below.

$$\{az+by+cx, bz+cy+dx, cz+dy+ex, dz+ey+fx, ez+fy+gx, fz+gy+hx, gz+hy+ix\} \quad (2)$$

If the kernel $\{x,y,z\}$ is replaced by $\{1, -2, 1\}$, the list convolution represents the second derivative of the original list and is given by equation (3) below.

$$\{a-2b+c, b-2c+d, c-2d+e, d-2e+f, e-2f+g, f-2g+h, g-2h+i\} \quad (3)$$

FIG. 2B shows the second derivative of FIG. 2A, where the second derivative is determined by the list convolution of the kernel [1, −2, 1] with the data in FIG. 2A. There are two fewer points in FIG. 2B than in FIG. 2A, due to the convolution. The result of having fewer points can be corrected for by padding values at the beginning and at the end. As examples, the added values can be equal to that of the second cycle or second to last cycle, or determined as a result of some functional fit, such as interpolation.

Other kernels can be used. For example, left-sided finite difference schemes can be used, where only previous cycles and the current cycle are used. For instance, respective values of (1, −2, 1) can be used at X−2, X−1, and X to obtain the second derivative at cycle X. Another example is the use of values (−1, 4, −5, 2) at X−3, X−2, X−1, and X. Similar kernels can be used in right-sided schemes, where only subsequent cycles and the current cycle are used. The example in equations (1)-(3) is of a central finite difference scheme, where one or more previous cycles, the current cycle, and one or more subsequent cycles are used. Another example of a central scheme is the use of values (−1, 16, −30, 16, −1) at X−2, X−1, X, X+1, and X+2. Additionally, small variations from these values can be used, e.g., (1.1, −2.05, 1.1). Embodiments are not limited to examples provided herein.

C. Results

Figures 4A, 4B:
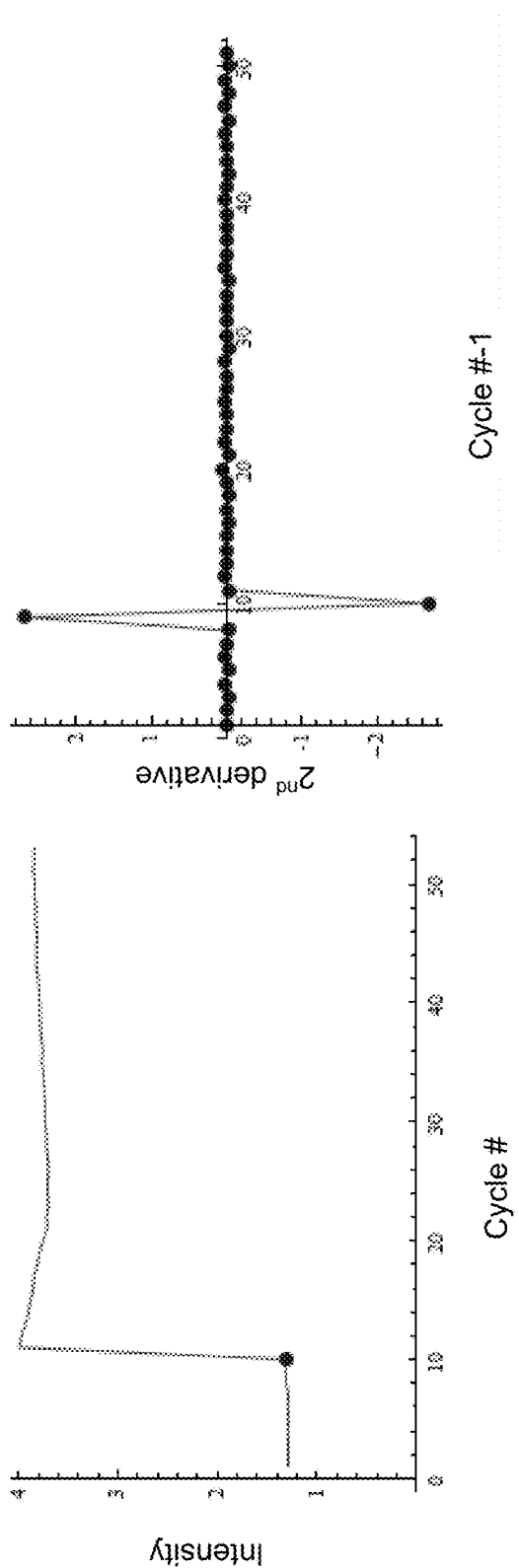
FIG. 4A shows actual Real-Time PCR data with a jump in an otherwise flat signal.
FIG. 4B shows the second derivative of the data from FIG. 4A

FIG. 4A shows actual Real-Time PCR data with a jump in an otherwise flat signal. FIG. 4B shows the second derivative of the data from FIG. 4A. The data in FIG. 4B is determined using the convolution for a central finite difference scheme. In FIG. 4A, the data decreases slightly after the jump, but generally remains relatively flat. Thus, this data set does not exhibit growth, as the only significant increase in the signal is due to the jump. If the jump were not identified, a false positive might occur in that the data set might be falsely identified as exhibiting growth. Such an incorrect analysis could result in an incorrect measurement of the underlying growth process for a biological sample. In FIG. 4B, as one can see, there is a pair of consecutive cycles (shown as X values of 9 and 10, which correspond to cycles 10 and 11) with a positive second derivative and a negative second derivative. These values also have the largest magnitude compared to the values at other cycles.

Figures 5A, 5B:
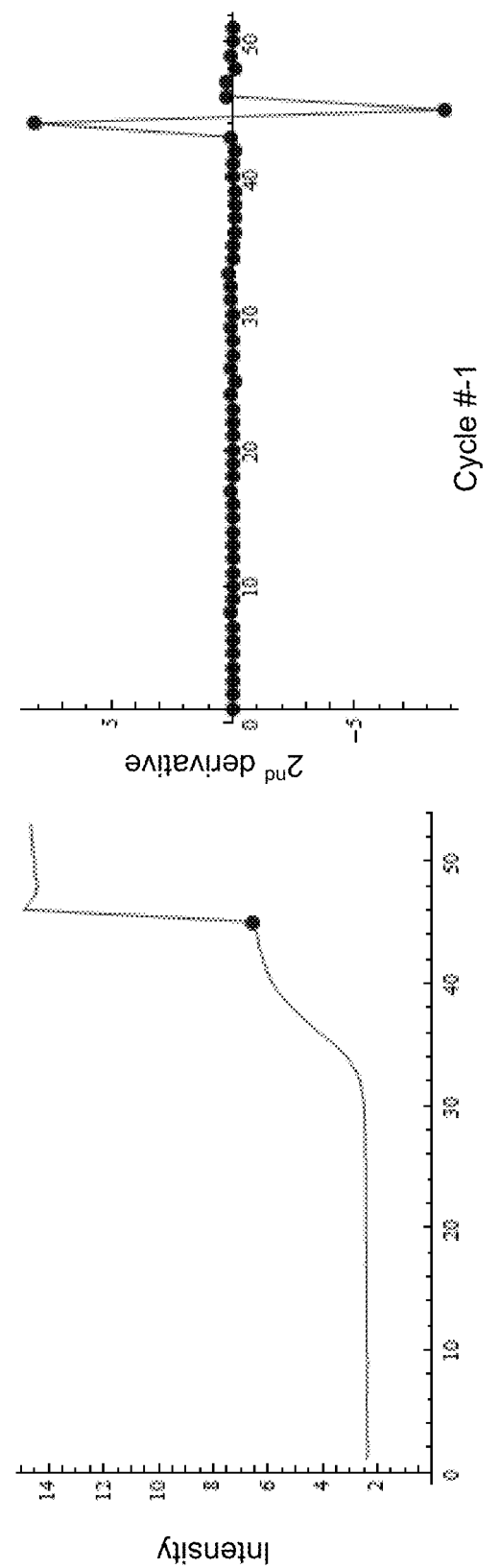
FIG. 5A shows actual Real-Time PCR data with a jump near the end of the exponential phase region.
FIG. 5B shows the second derivative of the data from FIG. 5A.

FIG. 5A shows actual Real-Time PCR data with a jump near the end of the exponential phase region. FIG. 5B shows the second derivative of the data from FIG. 5A. The data in FIG. 5B is determined using the convolution for a central finite difference scheme. FIG. 5A exhibits actual growth approximately between cycles 30 and 44. However, there is a jump at about cycle 45 that increases the signal from about 6 to over 14. This relatively large jump compared to the actual growth would skew any functional fit to the data. Thus, although qualitatively the functional fit would still identify that growth did occur in the underlying process, any quantitative data would be incorrect due to errors in the functional fit. In FIG. 5B, as one can see, there is a pair of consecutive cycles (shown as X values of 44 and 45, which correspond to cycles 45 and 46) with a positive second derivative and a negative second derivative. And, these values have a largest magnitude compared to the values at other cycles.

Figure 6B:
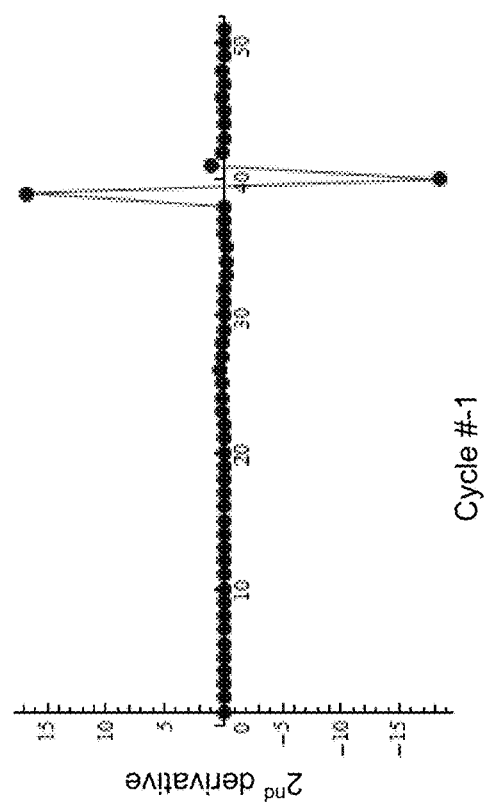
FIG. 6B shows the second derivative of the data from FIG. 6A.
Figure 6A:
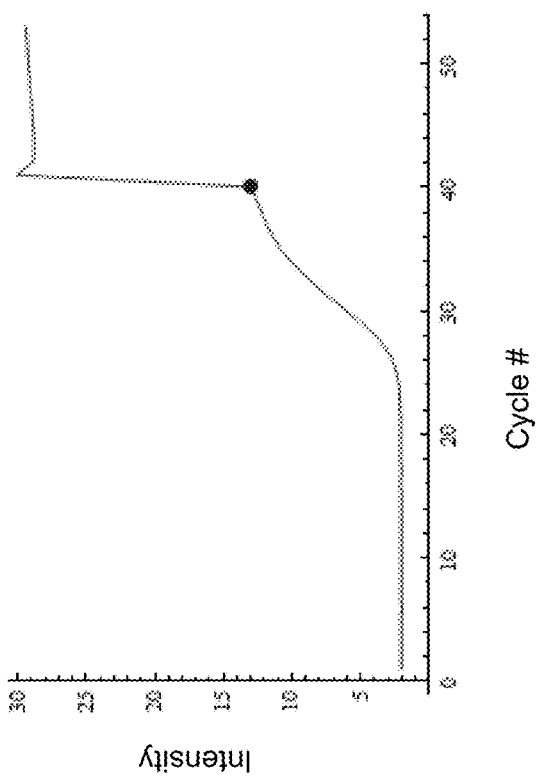
FIG. 6A shows actual Real-Time PCR data with a large jump near the end of the exponential phase region.

FIG. 6A shows actual Real-Time PCR data with a large jump near the end of the exponential phase region. FIG. 6B shows the second derivative of the data from FIG. 6A. The data in FIG. 6B is determined using the convolution for a central finite difference scheme. FIG. 6A exhibits actual growth approximately between cycles 26 and 40. However, there is a jump at about cycle 40 that increases the signal from about 14 to about 30. This relatively large jump compared to the actual growth would also skew any functional fit to the data. Thus, although qualitatively the functional fit would still identify that growth did occur in the underlying process, any quantitative data would be incorrect due to errors in the functional fit. In FIG. 6B, as one can see, there is a pair of consecutive cycles (shown as X values of 39 and 40, which correspond to cycles 40 and 41) with a positive second derivative and a negative second derivative. And, these values have a largest magnitude compared to the values at other cycles.

Figures 7A, 7B:
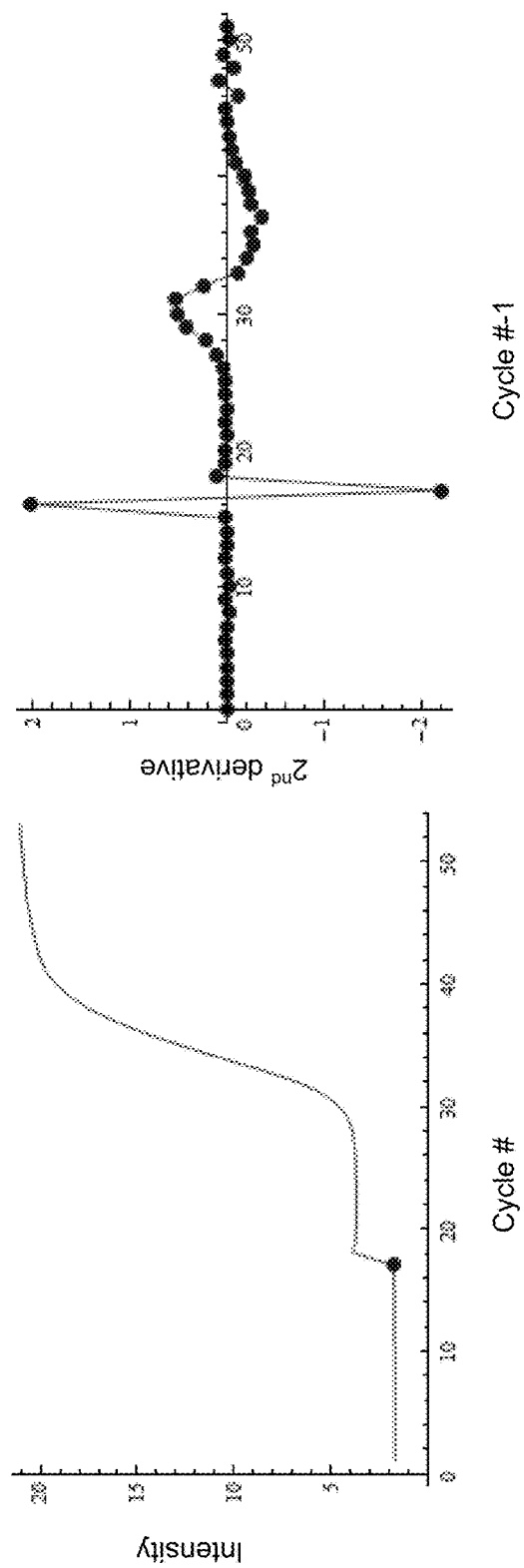
FIG. 7A shows actual Real-Time PCR data with a jump in a baseline region (i.e., before an exponential phase region) for a data set exhibiting growth.
FIG. 7B shows the second derivative of the data from FIG. 7A.

FIG. 7A shows actual Real-Time PCR data with a jump in a baseline region (i.e., before an exponential phase region) for a data set exhibiting growth. FIG. 7B shows the second derivative of the data from FIG. 7A. The data in FIG. 7B is determined using the convolution for a central finite difference scheme. FIG. 7A exhibits actual growth approximately between cycles 30 and 42. However, there is a jump at about cycle 17 that increases the signal from about 2 to about 4. This jump occurs before the exponential phase, but could be mistaken for the exponential phase. And, the jump could skew a determination of a baseline and skew any functional fit to the data. Thus, although qualitatively the functional fit would still identify that growth did occur in the underlying process, any quantitative data would be incorrect due to errors in the functional fit.

In FIG. 7B, as one can see, there is a pair of consecutive cycles (shown as X values of 16 and 17, which correspond to cycles 17 and 18) with a positive second derivative and a negative second derivative. And, these values have a largest magnitude compared to the values at other cycles. As the jump is not that large relative to the increase due to actual growth, FIG. 7B shows other second derivative values that are somewhat close to the second derivative values due to the jump. However, the second derivative values due to the jump are still significantly higher.

In each of the cases described, the jump is detected correctly by observing that there are two consecutive points in the second derivative graph, one positive and one negative, and that the magnitude of these points are the highest and lowest of all points in the graph. The jump occurs at 1 plus the X-value of the highest point.

D. Multiple Jumps

A data set could have multiple jump errors. In such a situation, one pair of consecutive cycles would have a larger magnitude than the pair of the other jump error. To detect and possibly correct for all jump errors, multiple passes could be made through the data. A minimum threshold for the magnitude could be used to ensure that spurious noise does not cause a very small positive second derivative value followed by a very small negative second derivative value in the next cycle to be identified as a jump error.

E. Negative Jumps

Although the examples shown are for positive jumps, negative jumps could also appear. A negative jump would cause the first cycle of the pair to have a negative second derivative value, and the second cycle of the pair would have a positive second derivative value. The analysis can still be implemented in a similar manner.

IV. Invalidation and Correction

Once a jump is detected, the jump and the data set can be analyzed to determine whether to invalidate the data set or correct the data set, or possibly whether neither should be done. Various criteria can be used to make these decisions. For example, a set of one or more invalidation criteria can be used to determine whether or not the data set should be invalidated. A set of one or more correction criteria can be used to determine whether or not the data set should be corrected. These criteria can be inputs into the computer system that analyzes the data. A determination of whether to invalidate or correct can be done at a time of collecting the data or at a later post-processing step.

Figure 8:
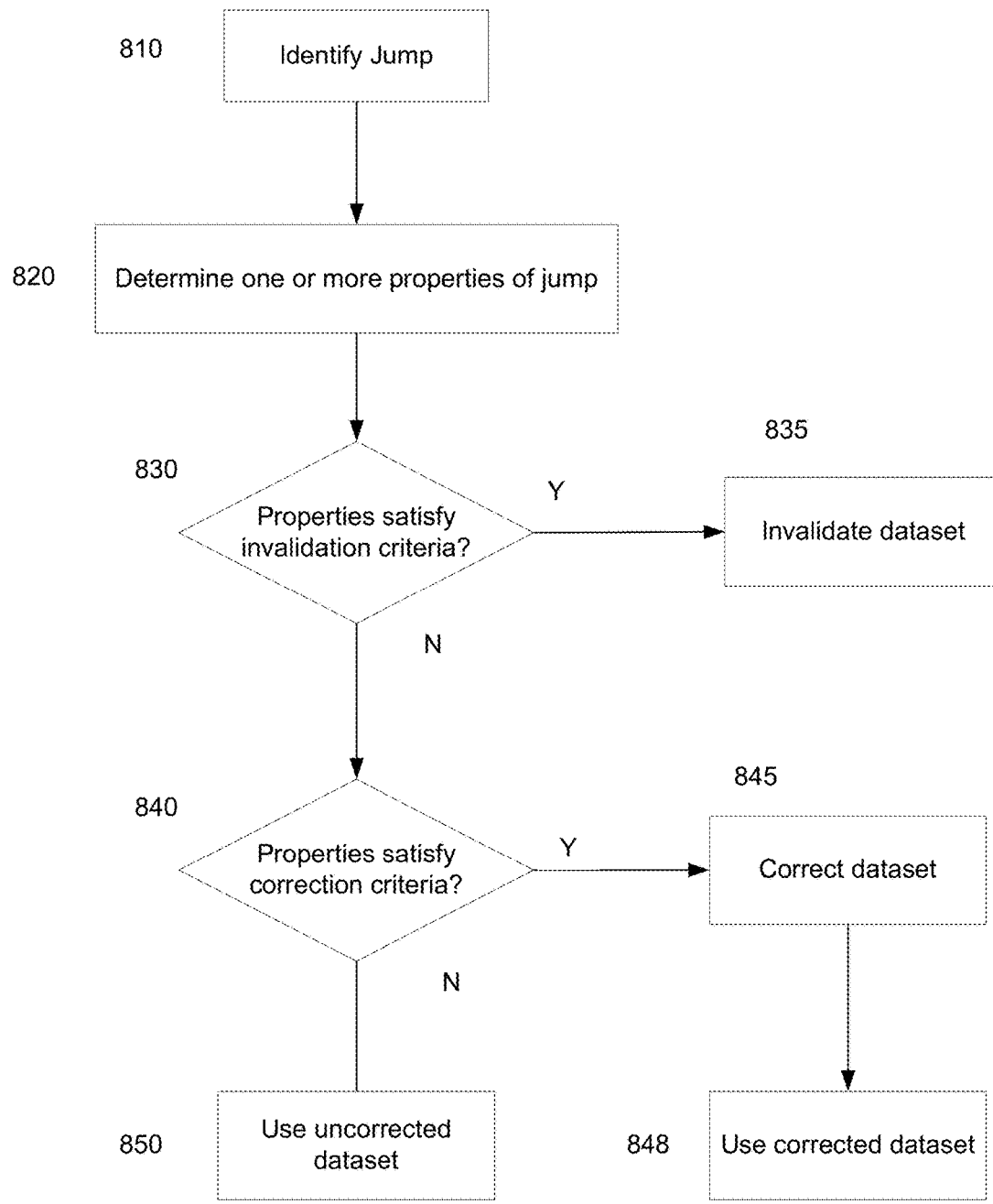
FIG. 8 is a flowchart of a method 800 for determining whether to invalidate the correct growth data had been identified jump error according to embodiments of the present invention.

FIG. 8 is a flowchart of a method 800 for determining whether to invalidate the correct growth data had been identified jump error according to embodiments of the present invention. Blocks of method 800 can be performed in various orders. For example, the decision as to whether to invalidate can be performed before or after a decision to correct the data. In some embodiments, invalidation and/or correction is always done.

At block 810, a jump is identified. For example, the jump can be identified using method 300. In one embodiment, the jump is identified for the data set, and a flag associated with the data set can be set to indicate that jump was detected. The existence of a flag can be used to prompt an analysis of the data set as to whether or not to invalidate or correct the data set.

At block 820, one or more properties of the jump are determined. For example, a height of the jump can be determined by taking a difference in the signal values from the first cycle to the second cycle of the pair. In one implementation, the height can be determined as an absolute value or a relative value. For instance, the jump height can be compared to the baseline intercept or to the net growth, if an exponential phase exists. The net growth can be determined as the signal strength after the growth minus the jump, and potentially also minus the baseline. A location of the jump can also be determined. The location can also be determined as an absolute or relative value. For example, a relative distance between the jump and a location of a region within the growth curve can be determined. For instance, the other location can be a start or end of the elbow region, a start or end of a baseline region, or a start or end of an exponential region.

At block 830, it is determined whether the one or more properties satisfy one or more invalidation criteria. In one embodiment, the invalidation criteria can specify that any growth curve having a jump is invalidated. In this case, all growth curves with a jump would be invalidated, and the properties would not need to be determined. In other embodiments, the growth curve would only be invalidated if the jump had certain properties, such as a certain height and/or a certain location.

At block 835, if the invalidation criteria is satisfied, then the dataset is invalidated. In one implementation, if the growth curve is invalidated, then no correction would be performed. The growth curve can be marked as invalidated, where such a marking can appear on a display. Further, when growth curve is invalidated, then no further analysis would generally be performed on the invalidated growth curve.

At block 840, it is determined whether the one or more properties satisfy one or more correction criteria. In one embodiment, the correction criteria can specify that any growth curve having a jump is corrected. In this case, all growth curves with a jump would be corrected, and the properties would not need to be determined. Even if the growth curve is corrected, it could still be invalidated at a later time. In other embodiments, the growth curve would only be corrected if the jump had certain properties, such as a certain height and/or a certain location.

At block 845, if the correction criteria is satisfied, then the dataset is corrected. Further details regarding corrections are provided below. The dataset can be corrected immediately or marked for correction at a later time.

At block 848, the corrected dataset is used. For example, a functional fit can be determined for the data set. Further details of the calculation of a functional fit can be found in U.S. Pat. No. 8,265,879, which is incorporated by reference. The functional fit can be used to determine whether or not growth occurred. As another use, a quantitative value can be determined from the functional fit. An example of a quantitative value is a $C_t$ value. The analysis and use of the corrected data set can be performed in a similar manner as situations when no jump was ever detected. Further details of the calculation of the $C_t$ value can be found in U.S. patent application Ser. No. 13/633,813 and U.S. Pat. No. 8,219,366, which are incorporated by reference.

At block 850, if none of the properties satisfied the invalidation criteria or the correction criteria, the corrected data set can be used. For example, if the jump was very small and at the beginning of the baseline, any errors due to the jump could be relatively small. Thus, one could use the uncorrected data set without too much sacrifice in accuracy.

A. Criteria for Invalidation and/or Correction

As mentioned above, various criteria can be used to determine whether or not to invalidate or correct growth data exhibiting a jump. For example, the magnitude of the jump height or magnitude relative to the net growth (e.g., total growth minus jump height), magnitude relative to baseline intercept, and cycle number of the jump might be used in the decision process to either invalidate or correct the growth curve.

Similar properties can be used for both validation and correction, but with different criteria being used. For example, if the jump height is higher than an invalidation threshold, then the growth data might be invalidated.

Whereas, if the jump height was lower than the invalidation threshold, but higher than a correction threshold, the growth data can be corrected.

The jump height can be compared to other values, such as the baseline value or net growth. For example, a ratio or difference can be calculated between the jump height and the other value. The ratio or the difference can then be compared to a threshold.

As another example, the location of the jump can be used. For example, if the jump was too close to the $C_t$ value (where an expected or estimated $C_t$ value can be known), then the growth data can be invalidated because it would be too difficult to obtain an accurate $C_t$ value given the jump's location. However, if the location was relatively far from an expected $C_t$ value, the growth data can be identified as being correctable, and a correction procedure can be performed.

Further, an early jump (e.g., in the baseline) is likely to be correctable. For example, if the real cases of $C_t$ are known to be around 20 or higher and the jump is at cycle 10, a determination can be made to correct the dataset. And, if the jump is late (e.g., in a plateau region), a determination can be made to correct the dataset.

In some embodiments, if the jump is so small then a determination can be made to not invalidate or correct the dataset. For example, if the jump height is about 0.1 (or other small threshold), then a jump error might be detected, or equivalently the jump is not invalidated or corrected.

B. Correction

The jump error can be corrected in various ways. One method to correct the data for the jump is to subtract the jump height from all data points subsequent to the jump. Another method is to add the jump height to all data points prior to the jump. An option after the jump correction is to shift to the left all fluorescence values subsequent to the corrected jump by one cycle number. This can prevent any discontinuity from appearing in the corrected jump curve. Such a shift may be beneficial when the jump occurs in an exponential phase (growth region).

As mentioned above, the jump height can be determined as the difference in the intensity between the two cycles. Since the location of the two cycles is identified by analyzing the second derivative, the intensities at the two cycles can be used to determine the jump height.

Regardless of the technique used, the correction would not alter the quantitative values, as a quantitative values is determined from relative intensity values, e.g., relative to a baseline. For example, the functional fit can have a constant, which does not affect a quantitative value (e.g., a $C_t$ value). The addition or subtraction of the jump height effectively only provides for a change in a constant, and thus the correction does not affect the quantitative results.

C. Correction Results

FIGS. 9-12 show growth curves having a jump and the corrected curves according to embodiments of the present invention. The growth curves correspond to FIGS. 4A, 5A, 6A, and 7A. As with the other plots, the vertical axis is intensity and the horizontal axis is cycle number.

Figure 9:
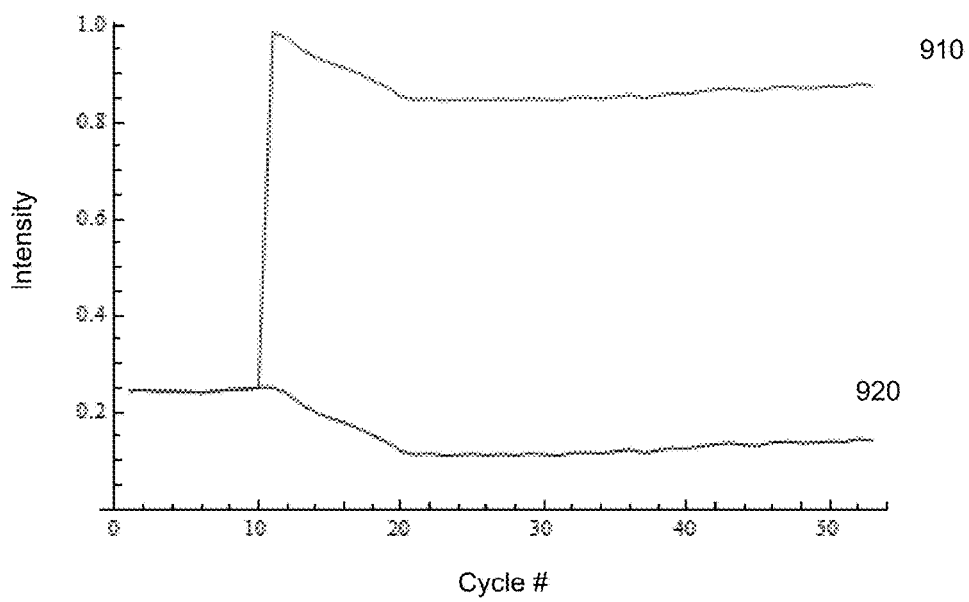
FIGS. 9-12 show growth curves having a jump and the corrected curves according to embodiments of the present invention.

FIG. 9 shows the raw data 910 and the corrected data 920. The corrected data 920 is generally flat, except for a small decrease between cycles 10 and 20. Corrected data 920 shows that no growth has occurred, and thus accurately reflects the physical process. The lack of growth can be identified in a subsequent processing step. The subsequent processing step can also identify the corrected data as having a decrease, which might occur from a negative control.

Figure 10:
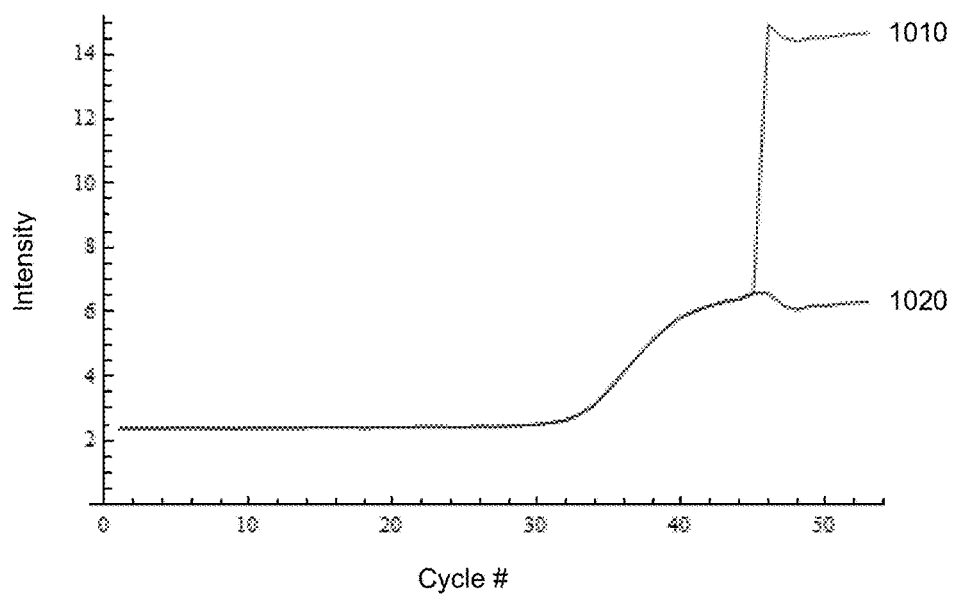

FIG. 10 shows the raw data 1010 and the corrected data 1020. The correction reduces the overall intensity in the plateau region to be in line with the end of the growth region. As with FIG. 9, a decrease is seen in both datasets after the jump. The amount of decrease in one growth curve (e.g., a control) can be used in the correction of other growth curves. In this manner, the correction can include an addition to the cycles immediately following the jump (i.e., after the jump height has been subtracted out).

Figure 11:
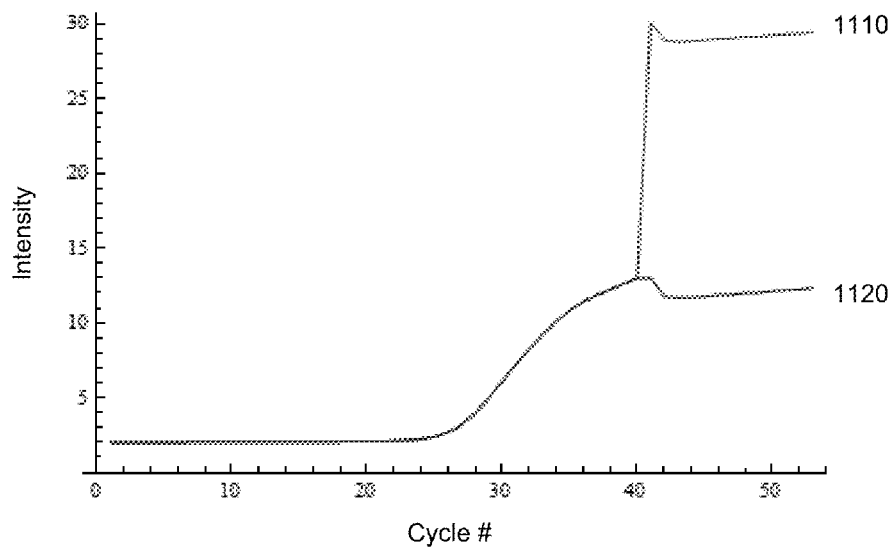

FIG. 11 shows the raw data 1110 and the corrected data 1120. As with FIG. 10, the correction reduces the overall intensity and the plateau region to be in line with the end of the growth region. The decrease after the jump can also be corrected, as mentioned above.

Figure 12:
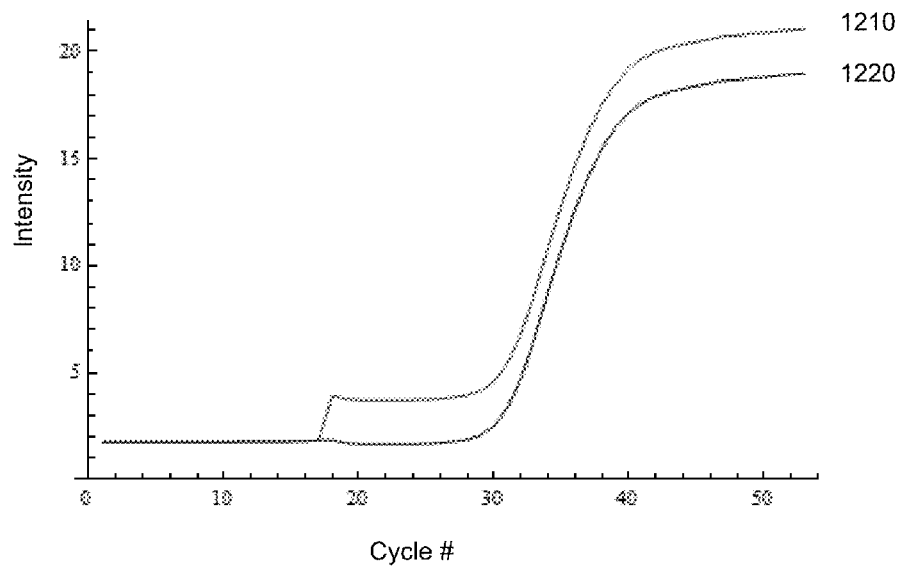

FIG. 12 shows the raw data 1210 and the corrected data 1220. The correction provides for a smooth baseline that leads to the growth region. Thus, an accurate functional fit can be obtained.

Figure 13:
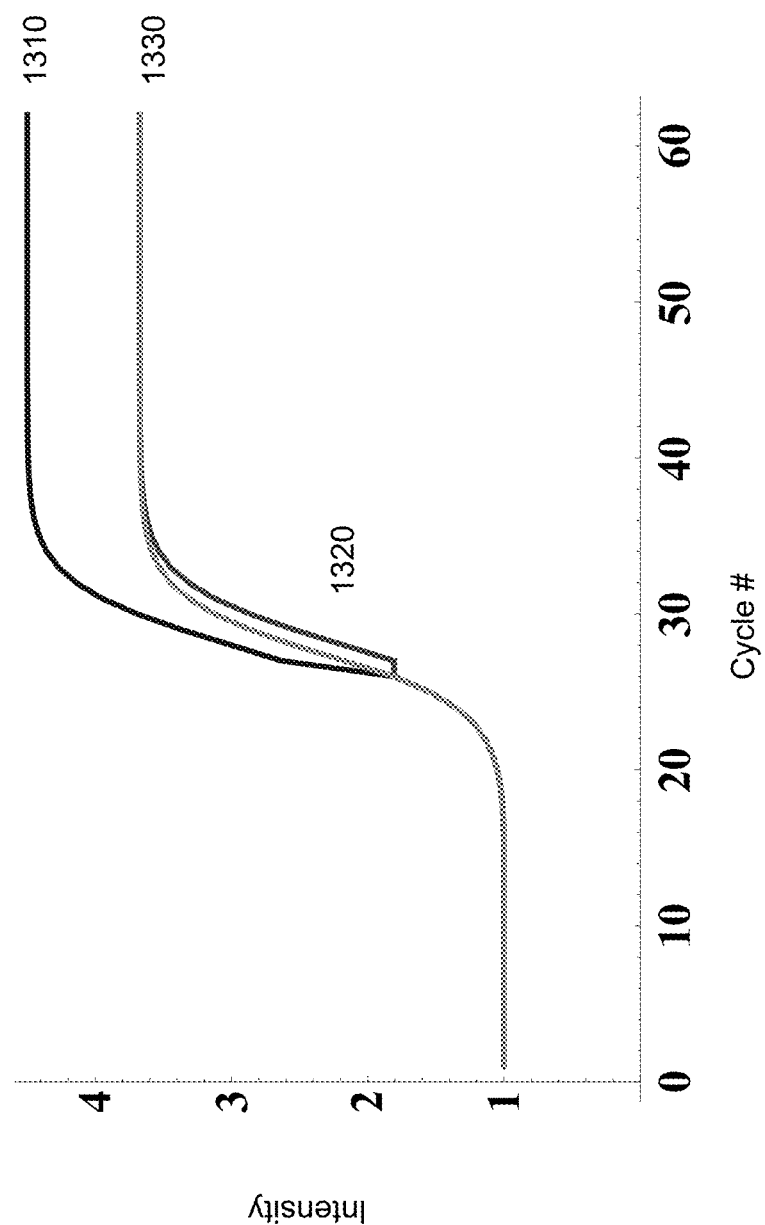
FIG. 13 shows a raw curve 1310 having a jump error, a height corrected curve 1320, and shift and height corrected curve 1330 according to embodiments of the present invention.

FIG. 13 shows a raw curve 1310 having a jump error, a height corrected curve 1320, and shift and height corrected curve 1330 according to embodiments of the present invention. Height corrected curve 320 has a discontinuity because the jump occurs during growth of the PCR curve. This discontinuity can be removed by shifting the intensity values subsequent to the jump by one cycle to the left. This is shown by the shift and height corrected curve 1330.

The discontinuity arises from the fact that the difference in intensity values from the first cycle to the second cycle of the jump have one contribution that is due to the error and another contribution that is due to the actual growth that is occurring. Thus, if the total difference is all attributed to the error, the second cycle is guaranteed to have the same intensity as the first cycle. The shifting brings the corrected curve back in line with the growth region.

In other embodiments, instead of shifting, an estimate can be made as to the actual amount of growth from the first cycle to the second cycle. For example, linear interpolation can be used to determine the expected signal value at the second cycle based on the signal values of cycles near the jump. This can provide an estimate for how much the actual increase is. Then, the increase attributable to the actual growth can be added back in after the total difference between the two cycles is subtracted out. Or equivalently, the growth increase can be subtracted from the total jump height to obtain the actual jump error.

V. Computer System

Figure 14:
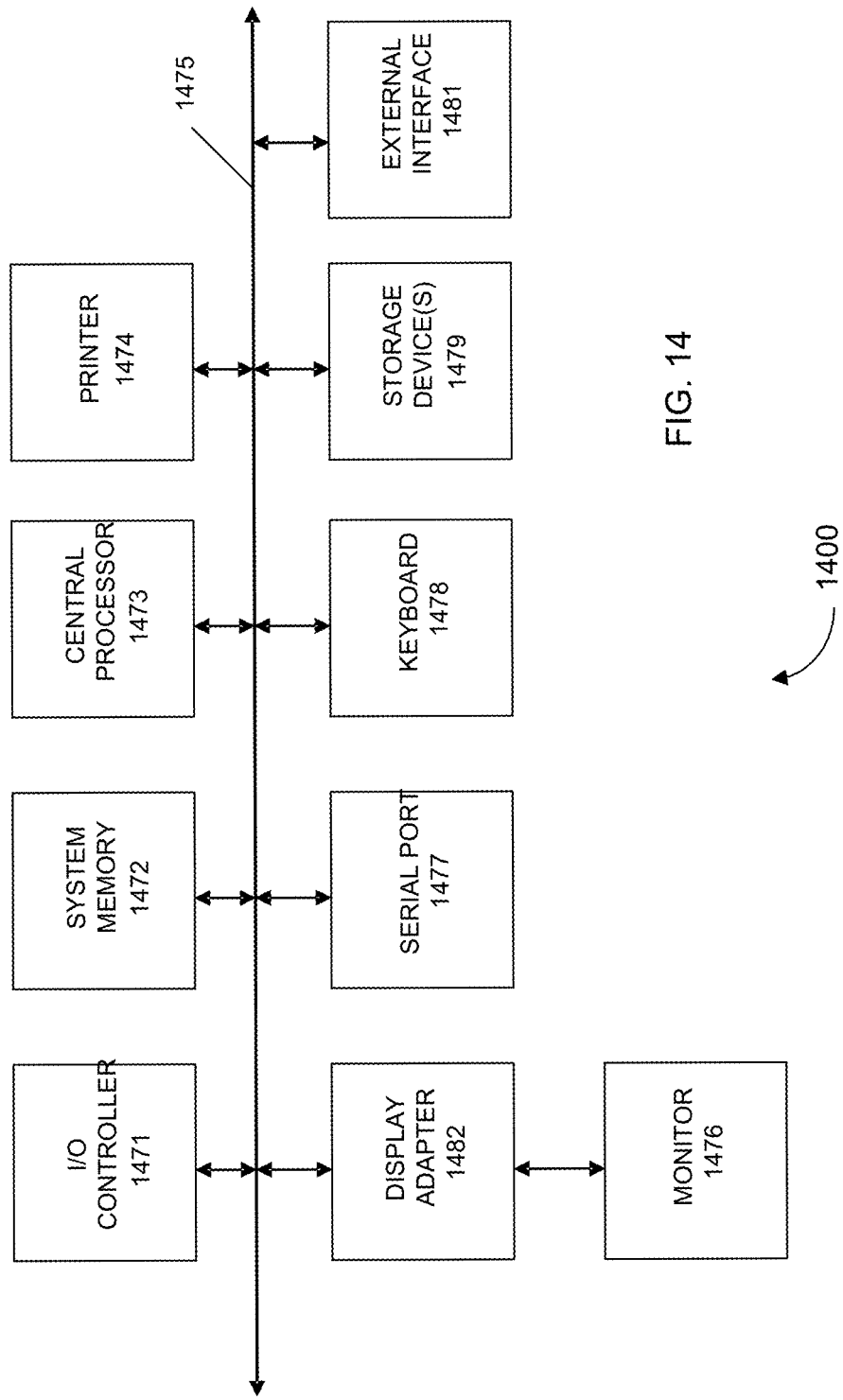
FIG. 14 shows a block diagram of an example computer system 1300 usable with system and methods according to embodiments of the present invention.

Any of the computer systems mentioned herein may utilize any suitable number of subsystems. Examples of such subsystems are shown in FIG. 14 in computer apparatus 1400. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 14 are interconnected via a system bus 1475. Additional subsystems such as a printer 1474, keyboard 1478, storage device(s) 1479, monitor 1476, which is coupled to display adapter 1482, and others are shown. Peripherals and input/output (I/O) devices, which couple to I/O controller 1471, can be connected to the computer system by any number of means known in the art, such as serial port 1477. For example, serial port 1477 or external interface 1481 (e.g. Ethernet, Wi-Fi, etc.) can be used to connect computer system 1400 to a wide area network such as the Internet, a mouse input device, or a scanner. The interconnection via system bus 1475 allows the central processor 1473 to communicate with each subsystem and to control the execution of instructions from system memory 1472 or the storage device(s) 1479 (e.g., a fixed disk), as well as the exchange of information between subsystems. The system memory 1472 and/or the storage device(s) 1479 may embody a computer readable medium. Any of the values mentioned herein can be output from one component to another component and can be output to the user.

A computer system can include a plurality of the same components or subsystems, e.g., connected together by external interface 1481 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As user herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive, a CD, or an entire computer system), and may be present on or within different computer program products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned here are incorporated by reference in their entirety for all purposes. None is admitted to be prior art.

What is claimed is:

1. A method of detecting jump errors in a growth curve of a growth process, the method comprising:
   receiving, at a computer system, a dataset representing a growth curve, the dataset including a plurality of data points, each data point having a pair of coordinate values of a cycle number and a signal strength of the growth process at the cycle number;
   calculating, by the computer system, a discrete convolution of a kernel with discrete data points in the dataset to obtain a second derivative of the dataset at the cycle numbers;
   identifying whether two consecutive cycle numbers have values for the second derivative that have different signs;
   when a first cycle number and a second cycle number respectively have a first value and a second value for the second derivative with different signs, determining whether a magnitude of at least one of the first value and the second value is greater than a threshold; and
   identifying that a jump error has occurred in the dataset representing the growth curve based on a determination that the magnitude of at least one of the first value and the second value is greater than the threshold.

2. The method of claim 1, further comprising:
   determining whether the magnitude of both the first value and the second value are greater than one or more thresholds,
   wherein the identification that a jump error has is based on a determination that the magnitude of both the first value and the second value are greater than the one or more thresholds.

3. The method of claim 2, wherein the threshold tests whether the first value and the second value have a highest magnitude relative to other values for the second derivative.

4. The method of claim 1, wherein the threshold is a predetermined value.

5. The method of claim 1, wherein the first value is positive and the second value is negative.

6. The method of claim 1, further comprising:
determining one or more properties of the jump error; and
invalidating the dataset when the one or more properties of the jump error satisfy one or more invalidation criteria.

7. The method of claim 6, wherein the one or more invalidation criteria include at least one of:
a magnitude of the first value and/or the second value, and
a location of the jump error.

8. The method of claim 7, wherein the magnitude of the first value and/or the second value is relative to a baseline or a net growth in the dataset.

9. The method of claim 7, wherein the location of the jump error is relative to a location of a region of the growth curve.

10. The method of claim 7, further comprising:
correcting the dataset for the jump error.

11. The method of claim 10, further comprising:
determining one or more properties of the jump error, wherein the dataset is corrected when the one or more properties of the jump error satisfy one or more correction criteria.

12. The method of claim 11, wherein the one or more correction criteria include at least one of:
a magnitude of the first value and/or the second value, and
a cycle number of the jump error.

13. The method of claim 10, further comprising:
fitting a function to the corrected dataset; and
analyzing the fitted function to determine a property of the growth process.

14. The method of claim 10, wherein correcting the dataset includes:
identifying a location X of the jump error;
determining a height of the jump error; and
using the magnitude to correct the signal strength for cycle numbers before the jump error or to correct the dataset for cycle numbers after the jump error.

15. The method of claim 14, wherein correcting the dataset further includes:
shifting values of the signal strength for cycle numbers greater than X+2 to correspond to one cycle number less.

16. The method of claim 1, further comprising:
after identifying a jump error, searching the dataset for other locations where two consecutive cycle numbers have values for the second derivative that have different signs.

17. A computer product comprising a non-transitory computer readable medium storing a plurality of instructions that when executed control a computer system to detect jump errors in a growth curve of a growth process, the instructions comprising:
receiving a dataset representing a growth curve, the dataset including a plurality of data points, each data point having a pair of coordinate values of a cycle number and a signal strength of the growth process at the cycle number;
calculating a discrete convolution of a kernel with discrete data points in the dataset to obtain a second derivative of the dataset at the cycle numbers;
identifying whether two consecutive cycle numbers have values for the second derivative that have different signs;
when a first cycle number and a second cycle number respectively have a first value and a second value for the second derivative with different signs, determining whether a magnitude of at least one of the first value and the second value is greater than a threshold; and
identifying that a jump error has occurred in the dataset representing the growth curve based on a determination that the magnitude of at least one of the first value and the second value is greater than the threshold.

18. The computer product of claim 17, wherein the instructions further comprise:
determining one or more properties of the jump error; and
invalidating the dataset when the one or more properties of the jump error satisfy one or more invalidation criteria; and
correcting the dataset when the one or more properties of the jump error satisfy one or more correction criteria.

19. A Polymerase Chain Reaction (PCR) system, comprising:
a PCR data acquiring device that generates a PCR dataset representing a PCR amplification curve, said dataset including a plurality of data points, each having a pair of coordinate values of a cycle number and a signal strength of the growth process at the cycle number; and
an intelligence module adapted to process the PCR dataset to detect jump errors by:
calculating a discrete convolution of a kernel with discrete data points in the dataset to obtain a second derivative of the dataset at the cycle numbers;
identifying whether two consecutive cycle numbers have values for the second derivative that have different signs;
when a first cycle number and a second cycle number respectively have a first value and a second value for the second derivative with different signs, determining whether a magnitude of at least one of the first value and the second value is greater than a threshold; and
identifying that a jump error has occurred in the dataset representing the growth curve based on a determination that the magnitude of at least one of the first value and the second value is greater than the threshold.

20. The PCR system of claim 19, wherein the intelligence module is further adapted to:
determine one or more properties of the jump error; and
invalidate the dataset when the one or more properties of the jump error satisfy one or more invalidation criteria; and
correct the dataset when the one or more properties of the jump error satisfy one or more correction criteria.

* * * * *